(12) United States Patent  
Stewart

(10) Patent No.: US 9,060,679 B2  
(45) Date of Patent: Jun. 23, 2015

(54) ANIMAL HEALTH MONITORING SYSTEM

(71) Applicant: Allflex USA, Inc., DFW Airport, TX (US)

(72) Inventor: Robert Stewart, Boulder, CO (US)

(73) Assignee: ALLFLEX USA, INC., DFW Airport, TX (US)

( * ) Notice: Subject to any disclaimer, the term of this patent is extended or adjusted under 35 U.S.C. 154(b) by 0 days.

(21) Appl. No.: 14/257,710

(22) Filed: Apr. 21, 2014

(65) Prior Publication Data

US 2014/0336524 A1   Nov. 13, 2014

Related U.S. Application Data

(60) Provisional application No. 61/821,608, filed on May 9, 2013.

(51) Int. Cl.
| | |
|---|---|
| *G08B 23/00* | (2006.01) |
| *A61B 5/00* | (2006.01) |
| *A61B 5/01* | (2006.01) |
| *A61B 5/07* | (2006.01) |

(52) U.S. Cl.
CPC .............. *A61B 5/0015* (2013.01); *A61B 5/01* (2013.01); *A61B 5/073* (2013.01); *A61B 2503/40* (2013.01); *A61B 2560/0209* (2013.01)

(58) Field of Classification Search
CPC .................................................. A61B 5/0015
USPC ..................................................... 340/573.3
See application file for complete search history.

(56) References Cited

U.S. PATENT DOCUMENTS

| | | | |
|---|---|---|---|
| 6,342,839 B1* | 1/2002 | Curkendall et al. | 340/573.3 |
| 2004/0155782 A1* | 8/2004 | Letkomiller et al. | 340/573.3 |
| 2006/0114109 A1* | 6/2006 | Geissler | 340/539.13 |
| 2007/0001854 A1 | 1/2007 | Chung et al. | |
| 2007/0082613 A1 | 4/2007 | Cox | |

OTHER PUBLICATIONS

International Search Report and Written Opinion for International Application PCT/US14/34816, report completed Aug. 17, 2014, Mailed Sep 9, 2014, 5 Pgs., Sep. 9, 2014.

* cited by examiner

*Primary Examiner* — Kerri McNally
(74) *Attorney, Agent, or Firm* — KPPB LLP

(57) ABSTRACT

Systems and methods for animal health monitoring are described. In one embodiment, an animal health monitoring system includes a ruminant bolus transponder, a high frequency radio frequency transceiver device, and at least one base station including a high frequency radio frequency transceiver, wherein the high frequency radio frequency transceiver device is proximally located to the bolus transponder, wherein the ruminant bolus periodically emerges from a low power dormant state and measures data including at least one sensor measurement including time and date data, wherein the ruminant bolus is configured to store the measured data using the memory connected to the microcontroller in the ruminant bolus, wherein the ruminant bolus periodically emerges from a low power dormant state and transmits the stored data in the memory to the proximally located device via high frequency RF transmission, and wherein the ruminant bolus can be spontaneously activated by a low frequency scanner.

13 Claims, 3 Drawing Sheets

ANIMAL HEALTH MONITORING SYSTEM

CROSS REFERENCE TO RELATED APPLICATIONS

This application claims priority to U.S. Provisional Application Ser. No. 61/821,608, filed May 9, 2013, the entirety of which is hereby incorporated by reference.

FIELD OF INVENTION

This invention relates to the use of radio frequency identification and specifically to short range radio frequency communications applied to the remote monitoring of animal physiological data for the purpose of assessing animal health and welfare.

BACKGROUND

Various livestock identification methods are known and have been used for owner-ship marking and animal tracking purposes. Disease control, food safety, and supply chain management have produced regulations that mandate positive and unique identification. Herd population growth has necessitated development of automated identification technologies for management efficiency.

Radio Frequency Identification (RFID) is one such method of automated identification that has gained acceptance of regulatory agencies and is currently widely deployed. While several alternate RFID technologies exist, the passive transponder that operates at low frequency ("LF"—134.2 KHz) is the dominant type.

Early passive transponders included large electronic assemblies that were suspended from collars placed around animal necks, such as is depicted in FIG. 1 (104). As technology improved and application specific integrated circuits were developed, transponder form factors diminished. One current tagging method is an eartag (102) which usually includes a front section with visual marking, and a rear section retainer which houses the electronic passive transponder.

While an ear tag provide an effective means of unique identification, some agencies have adopted transponders encased in a bolus form factor, suitable for ruminant livestock. As shown in FIG. 1, the bolus (103) is placed in the ruminant's stomach, where it is retained for the duration of the animal's life. Installation in this location also provides the potential to collect animal physiological data, such as the animal's body temperature, and such applications have been disclosed in the prior art.

The passive transponder with temperature monitoring capability provides a useful means of unique identification and animal health monitoring, but is limited in several ways: (1) the animal must be proximal (typically within 1 meter) to a LF transponder scanner in order to collect identification and temperature data; (2) because the transponder has no integral power source, it cannot autonomously record temperature data for batch conveyance to the scanner at a later time; and (3) without sufficiently frequent temperature measurements, the value and significance of temperature data is greatly compromised.

SUMMARY OF THE INVENTION

Systems and methods for animal health monitoring are described. In one embodiment, an animal health monitoring system includes a ruminant bolus transponder including at least one physiological sensor, a microcontroller with memory, a low frequency radio frequency identification (RFID) transceiver, and a high frequency radio frequency transmitter, a high frequency radio frequency (RF) transceiver device including at least one physiological sensor, a microcontroller, and a high frequency radio frequency transceiver, and at least one base station including a high frequency radio frequency transceiver, wherein the high frequency radio frequency transceiver device is proximally located to the bolus transponder, wherein the ruminant bolus periodically emerges from a low power dormant state and measures data including at least one sensor measurement including time and date data, wherein the ruminant bolus is configured to store the measured data using the memory connected to the microcontroller in the ruminant bolus, wherein the ruminant bolus periodically emerges from a low power dormant state and transmits the stored data in the memory to the proximally located device via high frequency RF transmission, and wherein the ruminant bolus can be spontaneously activated by a low frequency scanner.

In another embodiment of the invention, the low frequency scanner configures the ruminant bolus to transmit the stored data.

In an additional embodiment of the invention, the low frequency scanner is configured to reconfigure the ruminant bolus.

In yet another additional embodiment of the invention, the low frequency scanner transmits configuration data and time/date synchronization to the ruminant bolus.

In still another additional embodiment of the invention, the high frequency radio frequency transceiver device emerges from a low power dormant state at intervals synchronous with the bolus transponder and the high frequency radio frequency transceiver device receives at least one piece of data via high frequency RF transmission.

In yet still another additional embodiment of the invention, the high frequency radio frequency transceiver device emerges from a low power dormant state and records data including at least one sensor measurement associated with current time and date in memory.

In yet another embodiment of the invention, the high frequency radio frequency transceiver device emerges from a low power dormant state at intervals synchronous with the at least one base station and the high frequency radio frequency transceiver device transmits stored data records including bolus transponder data and proximal device data via high frequency transmission.

In still another embodiment of the invention, the low frequency scanner obtains data stored on the bolus identification number.

In yet still another embodiment of the invention, the low frequency scanner reads a bolus identification number and sensor data stored in the ruminant bolus.

In yet another additional embodiment of the invention, the base station broadcasts polling requests to at least one high frequency radio frequency transceiver device.

In still another additional embodiment of the invention, the base station is configured to broadcast via high frequency RF.

In yet still another additional embodiment of the invention, a polling request is addressed to at least one high frequency radio frequency transceiver device.

In yet another embodiment of the invention, the high frequency radio frequency transceiver device responds to the polling request by transmitting requested stored sensor data.

DETAILED DESCRIPTION OF THE INVENTION

Figure 1:
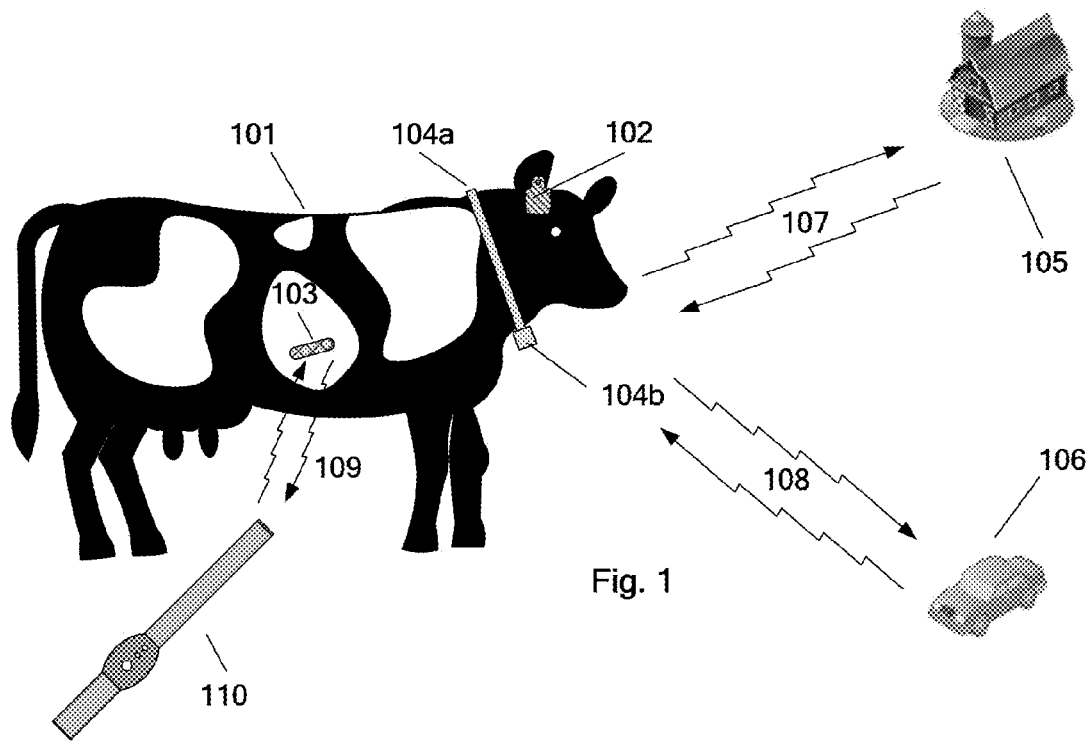
FIG. 1 illustrates pictorially the principal components of the present invention.

Turning now to the drawings, systems and methods for animal health monitoring are described. The present invention overcomes the disadvantages of the current art by providing a bolus transponder possessing (1) an integral power source that permits the autonomous collection of temperature data; (2) a real-time clock calendar (RTCC) that schedules data sample times and time/date stamps recorded temperatures; (3) means for temporary storage of collected temperature data; (4) means for scheduled conveyance of temperature data from the bolus to a proximally located high frequency (HF) radio frequency (RF) transceiver; (5) means for long range conveyance of temperature and identification data from the RF transceiver to a base station that collects data from one or more animal herds; and (6) bolus identification compatibility with standard low frequency scanners for close range data conveyance. In FIG. 1, the ruminant animal (101) possesses the bolus transponder (103), the proximally located high frequency RF transceiver (104b) suspended from a neck collar (104a), and an eartag (102) which may contain an electronic identification transponder as well as a visual marking. In practice, all 3 system components can be programmed to contain the same electronic identification (EID) number, typically an ISO compatible EID that has the decimal coded appearance "982 123456789012", for example. Identification and temperature data from each animal's health monitoring system is conveyed wirelessly via radio link (107, 108) to a base station (105) or to a mobile base station (106). Alternately, the bolus transponder (103) can communicate directly with a handheld (portable) or stationary low frequency scanner (110) via radio frequency link (109).

Bolus transponder (103) includes a cylindrical form factor, typically 21 mm in diameter and 70 mm in length, and is made of a material such as ceramic, which is not only biologically inert and hermetic, but which also imparts a suitable specific gravity to ensure retention in the animal's reticulum. The bolus contains an internal cavity of suitable volume to accommodate the bolus transponder's requisite electronic components. The bolus housing can be a two-piece assembly that fastens together, or it can be a one-piece assembly that is sealed with an epoxy after the transponder assembly has been deposited into its internal cavity.

Figure 2:
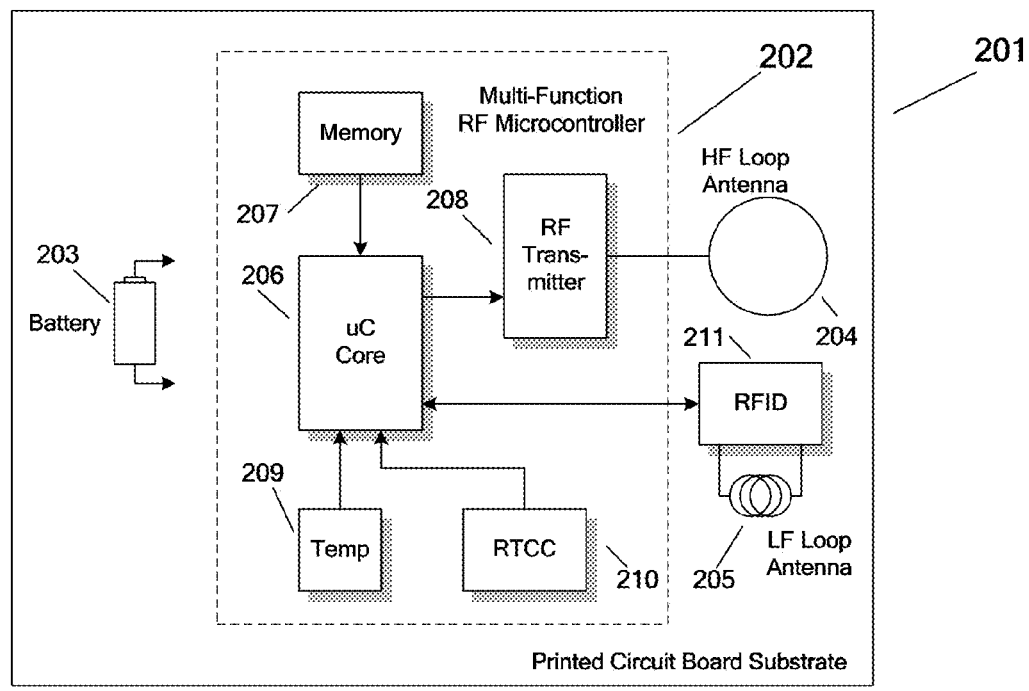
FIG. 2 presents a block diagram of the ruminant bolus electronic structure.

FIG. 2 illustrates schematically the architecture of the transponder. A printed circuit board (PCB) (201) provides a substrate carrier onto which the essential electronic components are electrically and mechanically attached.

A multi-function RF microcontroller (202) forms a first portion of the transponder's functional operation and control. Such devices are manufactured by integrated circuit companies such as Silicon Labs of Austin, Tex. A preferred component that fulfills the functional requirements of the bolus transponder is the Silicon Labs Si4010-C2 "SoC RF Transmitter." Other companies such as Texas Instruments and Microchip Corporation also make such multi-function "system-on-chip" microcontroller devices.

The Silicon Labs Si4010-C2 device is especially well suited for the bolus transponder in that it possesses all of the following capabilities: a 8051 microcontroller core (e.g. a processor), 4096 bytes RAM (random access memory), 8192 bytes NVM (non-volatile memory), a radio frequency (RF) transmitter (27 MHz-960 MHz), a real-time clock calendar (RTCC), a temperature sensor, single coin-cell battery operation (1.8-3.6 V), extremely low power consumption, and a small form factor (10-pin MSOP package). It should be noted, however, that any physiological sensor or sensors (i.e. any sensor that measures any data related to the health of a particular animal) can be employed within the bolus transponder and connected to the microcontroller as appropriate to the requirements of specific embodiments of the invention.

A low frequency radio frequency identification (RFID) device (211) forms a second portion of the transponder's functional operation and control. In the present invention, the Texas Instruments TMS37157 is a preferred component in that it is compatible with existing ISO 11784/85 HDX transponder standards, and provides enhanced capabilities, including a Serial Peripheral Interface (SPI) which accommodates connection to a microcontroller (such as the Si4010-C2), and power management modes suitable for controlling the activity of the composite transponder.

In addition to the multi-function RF microcontroller (202) and the RFID interface (211), the PCB substrate (201) also accommodates a battery (203), a low frequency (LF) loop antenna (205), and a high frequency (HF) loop antenna (204).

Battery (203) is preferably a lithium coin-cell or cylinder type battery whose size and capacity is determined by the power requirements of the microcontroller (202) and the required service life that the bolus must deliver.

HF loop antenna (204) typically includes an etched conductor path on the PCB substrate, although other form factors (such as a helically wound coil) are possible.

LF loop antenna (205) typically includes a conventional ferrite core wire wound antenna of the same type used in the manufacture of low frequency passive transponders.

The multi-function RF microcontroller (202) possesses several capabilities, among which those essential to the transponder bolus of the present invention are an RF transmitter (208), memory (207), microcontroller (uC) core (206), temperature sensor (209), and real time clock calendar (RTCC) (210). In an alternate scenario, other functions such as an analog-to-digital (ND) converter may exist to provide interfacing to additional physiological sensors.

The microcontroller (uC) core (206) functions in a conventional manner using stored program control to implement the several functions of the transponder bolus. The memory (207) portion retains the stored program control firmware and certain transponder data in non-volatile memory, and retains temperature measurements and time/date information in random access memory.

Temperature sensor (209) provides the ruminant's internal body temperature information to the microcontroller (206), and the RTCC (210) provides time/date information concurrent with the instance when temperature data is collected.

RF Transmitter (208) receives identification, temperature, and time/date data from the microcontroller (206) at scheduled intervals, and transmits this information over near range to the proximally located RF transceiver (104b) via HF loop antenna 204.

When interrogated using a conventional low frequency ISO 11784/85 scanner, the scanner's activation signal is received by LF loop antenna (205), and RFID device (211)

provides instantaneous identification data to the scanner. Additionally, an LF scanner with enhanced capabilities can collect identification, animal temperature, environmental temperature, time/date, and other data from the transponder bolus. An enhanced LF scanner can also impart data and configuration parameters to the transponder. Examples of such imparted data are the bolus transponder identification code (which can match the animal's eartag number), time/date synchronization, the scheduled intervals when data is transmitted from the transponder bolus, and other animal specific information. These data types are stored in non-volatile memory (207).

Figure 3:
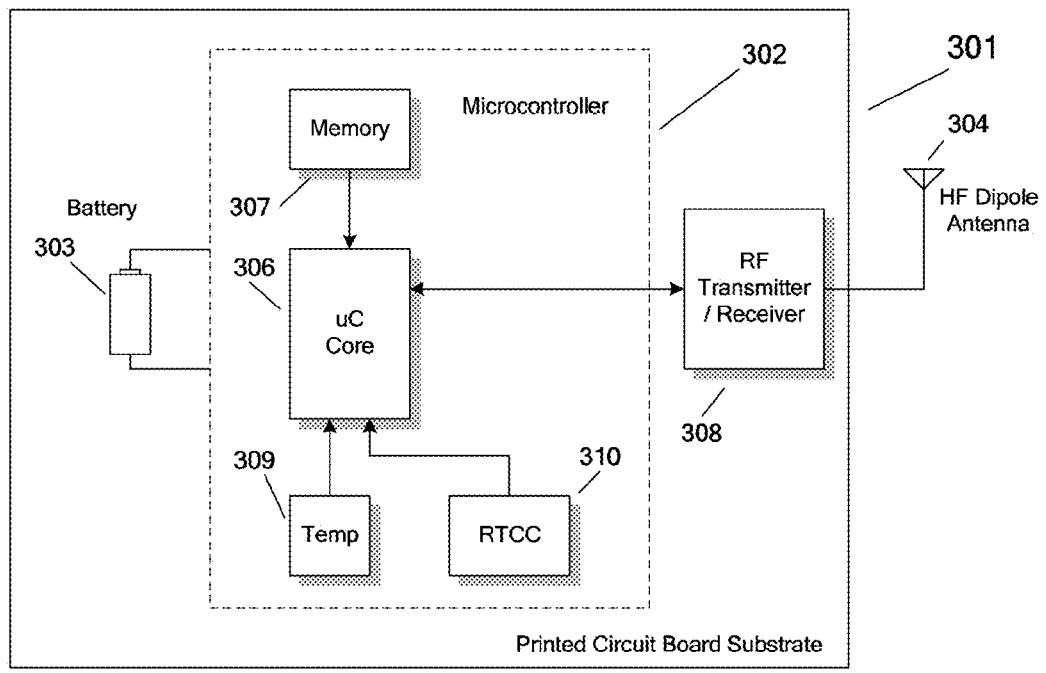
FIG. 3 presents a block diagram of the high frequency RF transceiver used to relay data to a base station.

FIG. 3 illustrates schematically the architecture of the proximally located RF transceiver (104b). This RF transceiver, which can be located on an animal collar, includes a printed circuit board substrate (301) on which electronic components are electrically and mechanically connected. This electronic assembly is preferably encased in a rugged hermetic housing that is suited to the rigors of this application. Disassembly for replacement of battery (303) prolongs the utility of the device. This encased assembly can be mechanically suspended from a collar (104a) device attached around the animal's neck as shown in FIG. 1.

The RF transceiver (104b) requires both radio frequency transmit and receive capabilities that provide it the capability to (a) receive identification, time/date, and temperature data from the transponder bolus (103), (b) receive data conveyance requests from a distance host system (105), and (c) transmit data acquired from the bolus transponder (103) to a distant host system.

Typically an RF device having both transmit and receive capability includes a discrete integrated circuit function (is not integral with a microcontroller), but could exist in either discrete or integral form in the present invention. A preferred architecture for the collar RF transceiver (104b, 301) includes two integrated circuits: a microcontroller (302), and an RF transmitter/receiver (308). In the present invention, the functional requirements of the microcontroller can be satisfied with the C8051F810 device manufactured by Silicon Labs of Austin, Tex., and the RF transmitter/receiver functional requirements can be met with the MRF49XA RF transceiver manufactured by Microchip Corporation of Chandler, Ariz. The present invention is not functionally limited by the capabilities of these two specific component choices, as a wide variety of other device are capable of providing equal, lesser, or greater capability.

The microcontroller (302) uses stored program control firmware retained in a non-volatile portion of memory (307) to execute its function as a data relay between the transponder bolus (103) and base station (105). The microcontroller also has a temperature sensor (309) that senses environmental temperature and RTCC (310) for time/date stamping data transmissions. In practice, the RF transceiver's RTCC can be periodically time/date synchronized via transmissions from the base station (105).

Figure 4:
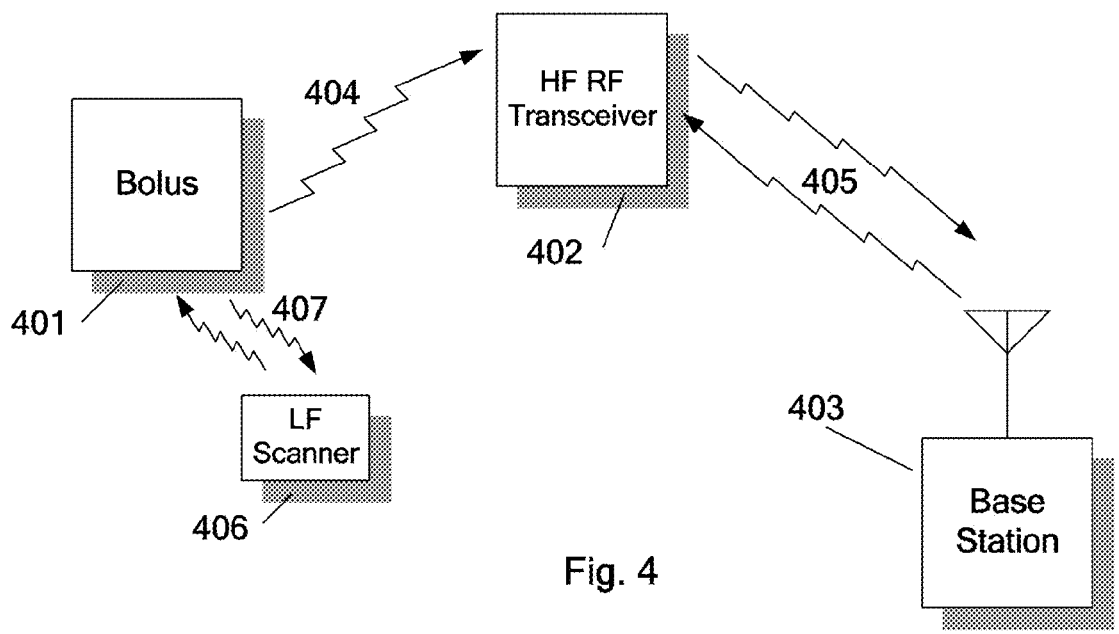
FIG. 4 presents a block diagram illustrating data conveyance among the system components.

The animal health monitoring system components are illustrated schematically in FIG. 4. Bolus transponder (401) has been programmed with a unique animal identification, time/date, data reporting interval, and other animal specific information prior to insertion into the ruminant animal. Part or all of this programmed data can be changed or updated using modulated activation signal transmission (407) sent to the bolus transponder from a low frequency scanner (406).

Once programmed and deployed in the animal, the bolus transponder (401) resides primarily in a low power dormant state. As determined by the programmed data collection parameters, the bolus transponder (401) periodically exits its dormant state, acquires temperature data from its internal sensor, adds a time/date stamp acquired from its internal RTCC, and stores this data record in its internal memory. For example, the bolus transponder could be programmed to execute this procedure once every hour.

After several data records have been stored in the bolus transponder's memory, programmed data collection parameters determine when these records are conveyed via short-range high frequency radio frequency (404) to the collar RF transceiver (402). RF transceiver (402) has been configured with the bolus transponder's identification number so that the data transmission is known to be from the paired bolus, and not from another nearby animal whose bolus transponder's transmission range might overlap. Transfer of multiple temperature data records could occur, for example, every 8 hours.

Collar RF transceiver (402) receives identification, temperature, and time/date data from bolus transponder (401) and stores it internally in memory. In a preferred embodiment, this data is retained by the RF transceiver (402) until solicited by base station (403). Collar RF transceiver can by itself collect periodic environmental temperature measurements and store these with time/date stamps, thereby retaining two data sets: that of the animal's body temperature, and that of the environmental temperature. These two data sets can be associated using the time/date stamp data associated with each.

Base station (403) is configured to periodically poll all animals in the herd in order to collect animal health data. Such polling is conducted using several different transmission channels and/or embedding the animal identification number in the polling request. This latter data acquisition method ensures that each animal is accounted for and avoids data transmission collisions that might otherwise occur if RF transceivers autonomously sent data at random times. For example, the base station could poll the RF transceiver once every 24 hours within a scheduled time slot. Alternately, the collar RF transceiver (402) can initiate communication with the base station (403) at scheduled intervals and convey data.

In a typical scenario, base station (403) transmits an RF signal (405) which is received by all herd animals. Each animal's RF transceiver (402) inspects the transmission for the embedded identification number, and the RF transceiver with the matching identification number answers the polling request by sending its stored temperature data to the base station (403). If any animal's RF transceiver fails to respond, the polling request can be repeated until a response is received. Furthermore, a missing animal alert could be issued to the herd manager. These polling requests can also include time/date synchronization signals so that all RF transceivers (402) in the herd remain synchronized. Such data acquisition requests can be scheduled once each day, for example. In power conserving mode, the collar RF transceiver (402) can wake-up at scheduled intervals to prepare for base station (403) polling queries In an alternate scenario, identification, temperature, and time/date data can be acquired directly from the bolus transponder by a low frequency (LF) scanner. For example, a dairy herd's data could be acquired in this fashion at times the herd enters the milking facility. In this derivative system, only the bolus transponder and LF scanner (406) are requisite system components.

In an alternate configuration wherein the livestock population is confined to within a physically small region, the bolus transponder can communicate directly with the base station without the proximal HF transceiver performing a communication relay service. In this arrangement, data transmission can be scheduled, or can be triggered upon receipt of a LF scanner activation command.

In yet another alternate scenario, identification, temperature, and time/date data can accumulate in the collar RF transceiver (402) over prolonged periods, and be acquired by a mobile base station (106) that travels from herd vicinity to herd vicinity.

Figure 5:
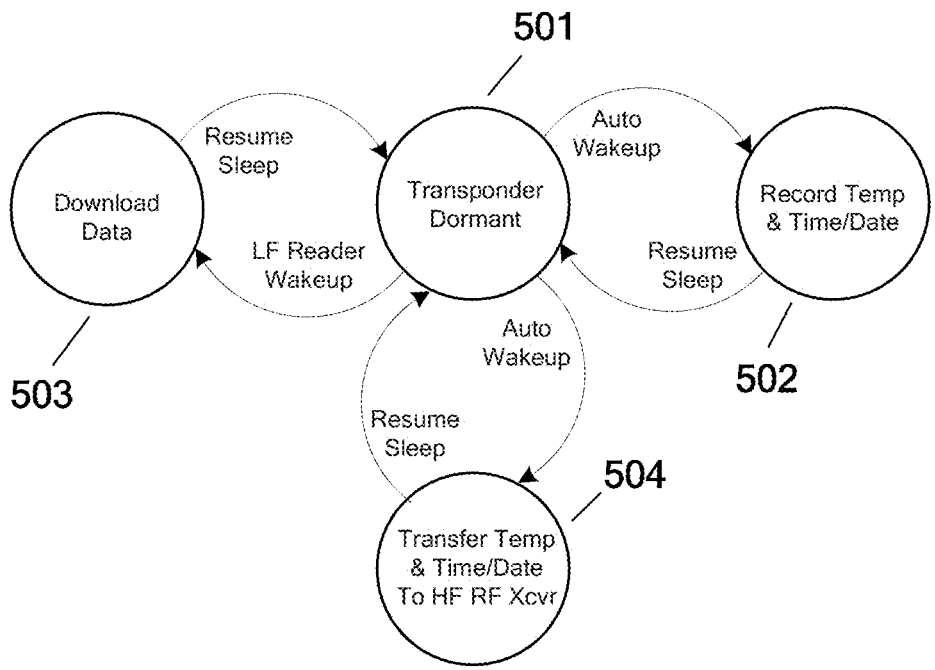
FIG. 5 is a state diagram illustrating the functional operation of the ruminant bolus transponder of the present invention.

FIG. 5 presents a state diagram that depicts the operational behavior of the bolus transponder. Because the bolus resides in the animal's reticulum, its battery must last the life span of the animal. Consequently, the bolus transponder electronics reside predominantly in a low power dormant state (501). In dormant state (501), the bolus RTCC function and LF wakeup stimulus remain enabled.

The bolus transponder can exit its dormant state in one of two ways: (1) at prescribed periodic intervals set by stored configuration data (e.g., "Auto Wakeup," or (2) upon receipt of an activation signal sent from a low frequency RFID reader (e.g., LF Reader Wakeup").

LF Reader activates the bolus transponder in a manner similar to conventional passive RFID operational technique, and can, in the present invention, be limited to acquiring only the transponder's identification code. The LF Reader transmits a signal having sufficient power to activate a portion of the bolus transponder electronics that permits the transponder to become self-powered by its internal battery. Configuration data previously set in the transponder, in conjunction with commands received from the LF Reader determine the content and format of the Download Data (503). Upon completion of data transfer, the bolus transponder resumes its dormant state (501).

Configuration data previously set in the transponder specifies an interval and/or a specific time/date at which the transponder's internal RTCC function invokes a wakeup command that causes the transponder to power up. The transponder enters a temperature recording state (502) during which temperature data from the transponder's internal sensor, and the current time/date, are stored as a data record in internal memory. Upon completion of this recording task, the transponder returns to its dormant state (501).

Configuration data previously set in the transponder also specifies a second interval and/or a second specific time/date at which the transponder's internal clock/calendar function invokes a wakeup command which causes the transponder to power up, and transmit identification code, temperature, and time/date records (504) to the RF transceiver where this information is stored until transferred to the base station. Upon completion of this data transfer task, the transponder returns to its dormant state (501).

Because the bolus RTCC function and the HF transceiver RTCC function operate independently, loss of time synchronization can eventually occur. The bolus transponder can include within the data transfer packet its instantaneous time/date, which the RF transceiver compares to its time/date, and calculates a correction factor that can revise the time/date records received from the bolus. When in communication with a LF scanner, the bolus time/date can be reset.

Figure 6:
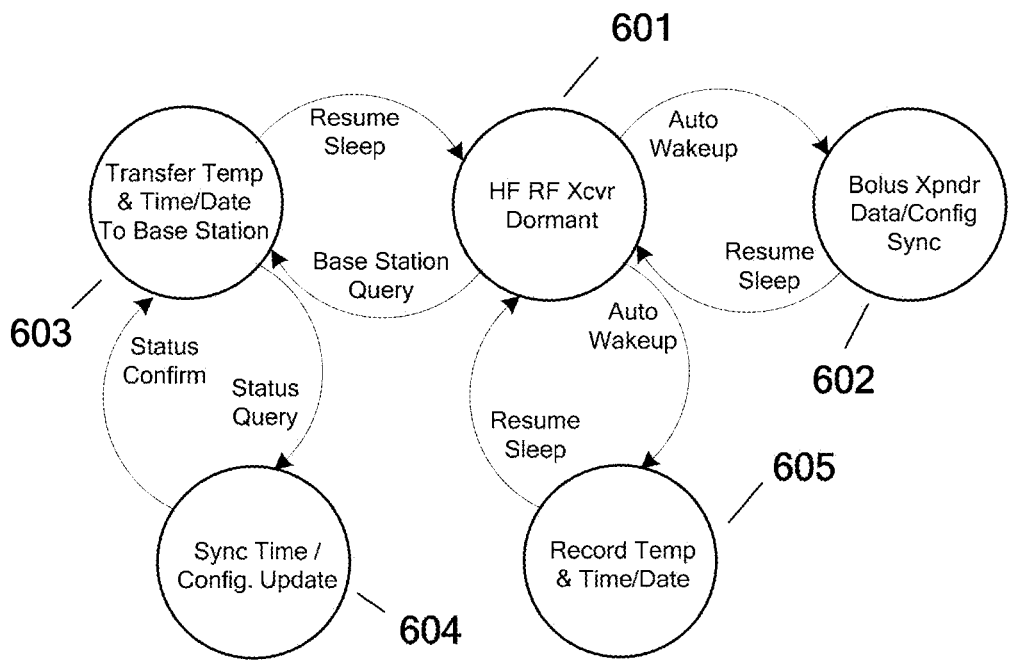
FIG. 6 is a state diagram illustrating the functional operation of the high frequency RF transceiver of the present invention.

FIG. 6 presents a state diagram that depicts the operational behavior of the RF transceiver. In order to conserve power and prolong battery life, the RF transceiver resides primarily in a low-power dormant state, and becomes active at scheduled time intervals. With the bolus transponder and RF transceiver clock/calendars synchronized, the RF transceiver enables its receive function during a time window that ensures capture of the bolus data (602). For example, if data transfer is scheduled to occur on the hour, the RF transceiver could enable its receiver 1 minute early, and remain enabled for 1 minute past the hour (or until bolus data is received. In the event no data transfer occurs, the RF transceiver stores an error flag that is conveyed to the base station at a later time.

Similarly, the RF transceiver uses a time scheduled activation to enable an environmental temperature recording with time/date stamping (605), whereupon completion the RF transceiver resumes its dormant state.

When scheduled for being queried by the base station (403), again the RF transceiver enables its receiver and awaits receipt of a polling signal containing its unique identification address, whereupon it transfers the previously acquired bolus data records along with its own data records. During connection with the base station (403), the RF transceiver may also acquire time synchronization and configuration updating from the base station. At completion of these data exchanges, the RF transceiver resumes its dormant state (601) until scheduled to conduct another data acquisition or data transfer task.

In the event the RF transceiver fails to receiver a base station polling event when scheduled, an internal flag is set and associated with the data sets not transferred so that these data sets can be preserved and a transfer can be attempted at the next base station polling event.

Alternately, the RF transceiver can remain in a receiver enabled state so that base station polling can occur on an ad hoc basis rather than at predetermined scheduled times.

Although the present invention has been described in certain specific aspects, many additional modifications and variations would be apparent to those skilled in the art. For example, any of the various processes described above can be performed in alternative sequences and/or in parallel (on different computing devices) in order to achieve similar results in a manner that is more appropriate to the requirements of a specific application. Additionally, any other devices that can be configured to perform the processes described herein can be employed in a variety of embodiments of the invention. It is therefore to be understood that the present invention can be practiced otherwise than specifically described without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. An animal health monitoring system, comprising:
   a ruminant bolus transponder comprising at least one physiological sensor, a microcontroller with memory, a low frequency radio frequency identification (RFID) transceiver, and a high frequency radio frequency transmitter;
   at least one high frequency radio frequency (RF) transceiver device comprising at least one physiological sensor, a microcontroller, and a high frequency radio frequency transceiver; and
   at least one base station comprising a high frequency radio frequency transceiver;
   wherein the high frequency radio frequency transceiver device is proximally located to the ruminant bolus transponder;
   wherein the ruminant bolus transponder periodically emerges from a low power dormant state and measures data comprising at least one sensor measurement comprising time and date data;
   wherein the ruminant bolus transponder is configured to store the measured data using the memory connected to the microcontroller in the ruminant bolus;

wherein the ruminant bolus transponder periodically emerges from a low power dormant state and transmits the stored data in the memory to the proximally located device via high frequency RF transmission; and wherein the ruminant bolus transponder can be spontaneously activated by a low frequency scanner.

2. The animal health monitoring system of claim 1, wherein the low frequency scanner configures the ruminant bolus transponder to transmit the stored data.

3. The animal health monitoring system of claim 1, wherein the low frequency scanner is configured to reconfigure the ruminant bolus transponder.

4. The animal health monitoring system of claim 3, wherein the low frequency scanner transmits configuration data and time/date synchronization to the ruminant bolus transponder.

5. The animal health monitoring system of claim 1, wherein:
the high frequency radio frequency transceiver device emerges from a low power dormant state at intervals synchronous with the ruminant bolus transponder; and
the high frequency radio frequency transceiver device receives at least one piece of data via high frequency RF transmission.

6. The animal health monitoring system of claim 1, wherein the high frequency radio frequency transceiver device emerges from a low power dormant state and records data comprising at least one sensor measurement associated with current time and date in memory.

7. The animal health monitoring system of claim 1, wherein:
the high frequency radio frequency transceiver device emerges from a low power dormant state at intervals synchronous with the at least one base station; and
the high frequency radio frequency transceiver device transmits stored data records comprising ruminant bolus transponder data and proximal device data via high frequency transmission.

8. The animal health monitoring system of claim 1, wherein the low frequency scanner obtains data stored on the ruminant bolus transponder.

9. The animal health monitoring system of claim 1, wherein the low frequency scanner reads a bolus identification number and sensor data stored in the ruminant bolus transponder.

10. The animal health monitoring system of claim 1, wherein the base station broadcasts polling requests to at least one high frequency radio frequency transceiver device.

11. The animal health monitoring system of claim 10, wherein the base station is configured to broadcast via high frequency RF.

12. The animal health monitoring system of claim 11, wherein a polling request is addressed to at least one high frequency radio frequency transceiver device.

13. The animal health monitoring system of claim 11, wherein the high frequency radio frequency transceiver device responds to the polling request by transmitting requested stored sensor data.

\* \* \* \* \*